United States Patent
Goldau et al.

(10) Patent No.: US 7,077,819 B1
(45) Date of Patent: Jul. 18, 2006

(54) METHOD FOR DETERMINING THE DISTRIBUTION VOLUME OF A BLOOD COMPONENT DURING AN EXTRACORPOREAL BLOOD TREATMENT AND DEVICE FOR CARRYING OUT THE METHOD

(75) Inventors: Rainer Goldau, Werneck (DE); Thomas Graf, Schweinfurt (DE); Malte Gross, Würzburg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 09/868,950

(22) PCT Filed: Dec. 23, 1999

(86) PCT No.: PCT/EP99/10338

§ 371 (c)(1),
(2), (4) Date: Nov. 5, 2001

(87) PCT Pub. No.: WO00/38761

PCT Pub. Date: Jul. 6, 2000

(30) Foreign Application Priority Data

Dec. 24, 1998 (DE) ............................... 198 60 330

(51) Int. Cl.
*A61M 37/00* (2006.01)
*C02F 1/44* (2006.01)
(52) U.S. Cl. .................. 604/5.04; 604/6.09; 210/645; 210/646; 210/746; 210/195.2
(58) Field of Classification Search ........ 210/645–646, 210/739, 746, 96.2, 85, 321.75, 600, 649, 210/634, 651, 929, 500.21, 433.1, 321.65, 210/321.71; 604/6.09, 6.04, 6.11, 6.01, 4.01, 604/5.01, 5.04, 6.1; 600/366, 322, 368
See application file for complete search history.

(56) References Cited

U.S. PATENT DOCUMENTS 4,267,040 A    5/1981    Schal (Continued)

FOREIGN PATENT DOCUMENTS

DE    39 38 662    7/1981

(Continued)

*Primary Examiner*—Patricia Bianco
*Assistant Examiner*—Leslie R. Deak
(74) *Attorney, Agent, or Firm*—Kenyon & Kenyon LLP

(57) ABSTRACT

The invention relates to a method for determining the volume of distribution of a blood component in the body of a living organism, especially the volume of distribution of urea, during an extracorporeal blood treatment. According to this method, the blood to be treated flows through the blood chamber (3) of a dialysis machine (1) in an extracorporeal circuit, said dialysis machine being divided into said blood chamber and a dialysing liquid chamber (4) by a semipermeable membrane (2). Dialysing liquid flows through the dialysing liquid chamber of the dialysis machine in a dialysing liquid channel. The method is based on the determination of the temporal change in the concentration of the blood component in the blood upstream of the dialysis machine using the temporal variation in a physical or chemical characteristic of the dialysing liquid upstream and downstream of the dialysis machine and the determination of the volume of distribution of the substance in the body of a living organism using the temporal variation in the concentration of the blood component in the blood. The invention also relates to a device for the extracorporeal blood treatment, comprising a device for determining the volume of distribution of a blood component in the body of a living organism.

25 Claims, 2 Drawing Sheets

U.S. PATENT DOCUMENTS

Figure 1:
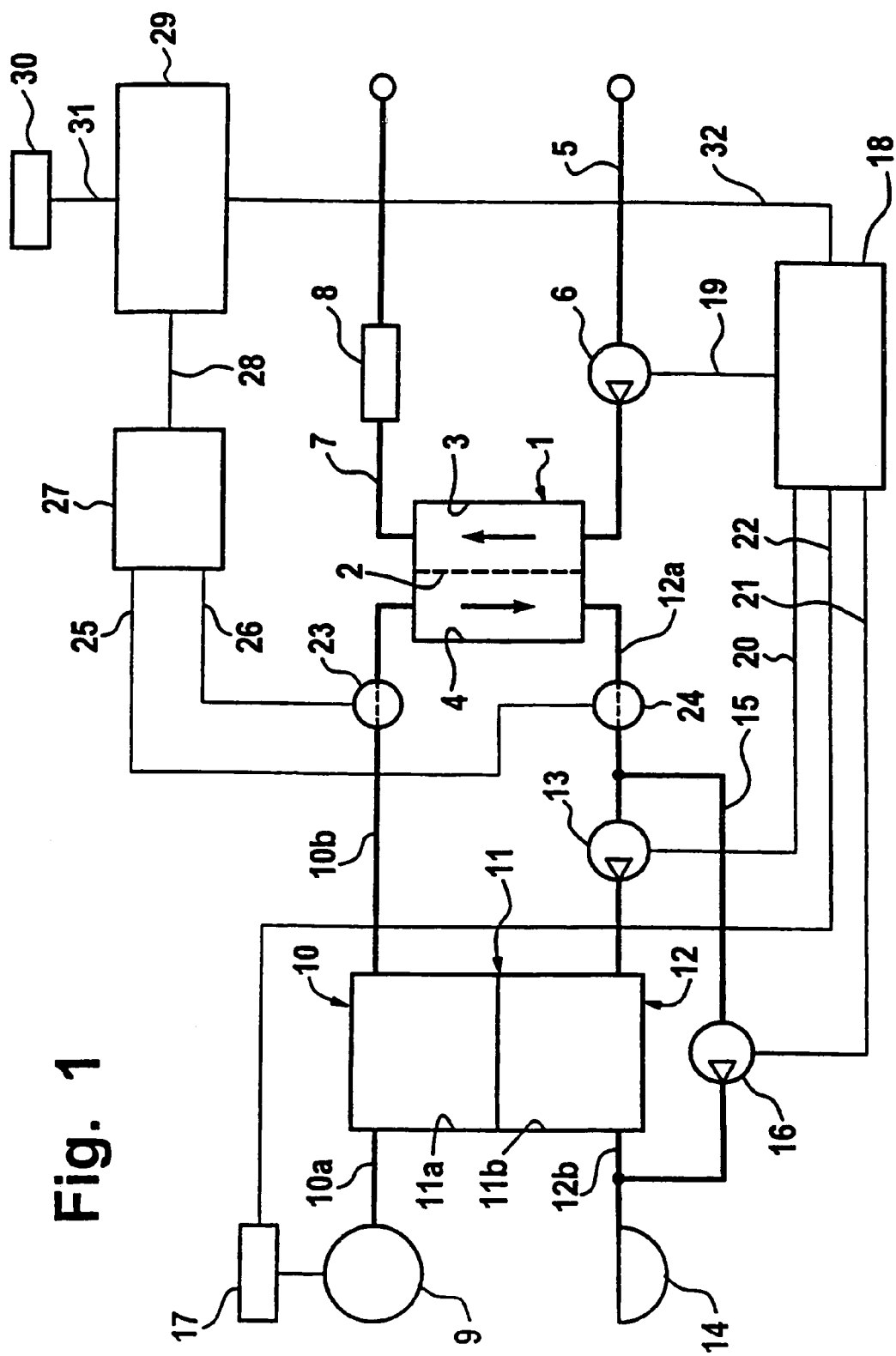

| | | | | |
|---|---|---|---|---|
| 5,252,213 A | * | 10/1993 | Ahmad et al. | 210/542 |
| 5,900,726 A | * | 5/1999 | Brugger et al. | 324/71.1 |
| 6,110,384 A | * | 8/2000 | Goux et al. | 210/739 |
| 6,156,002 A | * | 12/2000 | Polaschegg et al. | 604/4.01 |
| 6,258,027 B1 | * | 7/2001 | Sternby | 600/366 |

FOREIGN PATENT DOCUMENTS

| | | |
|---|---|---|
| EP | 330 892 | 9/1989 |
| EP | 291 421 | 11/1998 |
| WO | 98 55166 | 12/1998 |
| WO | 99 29355 | 6/1999 |

* cited by examiner

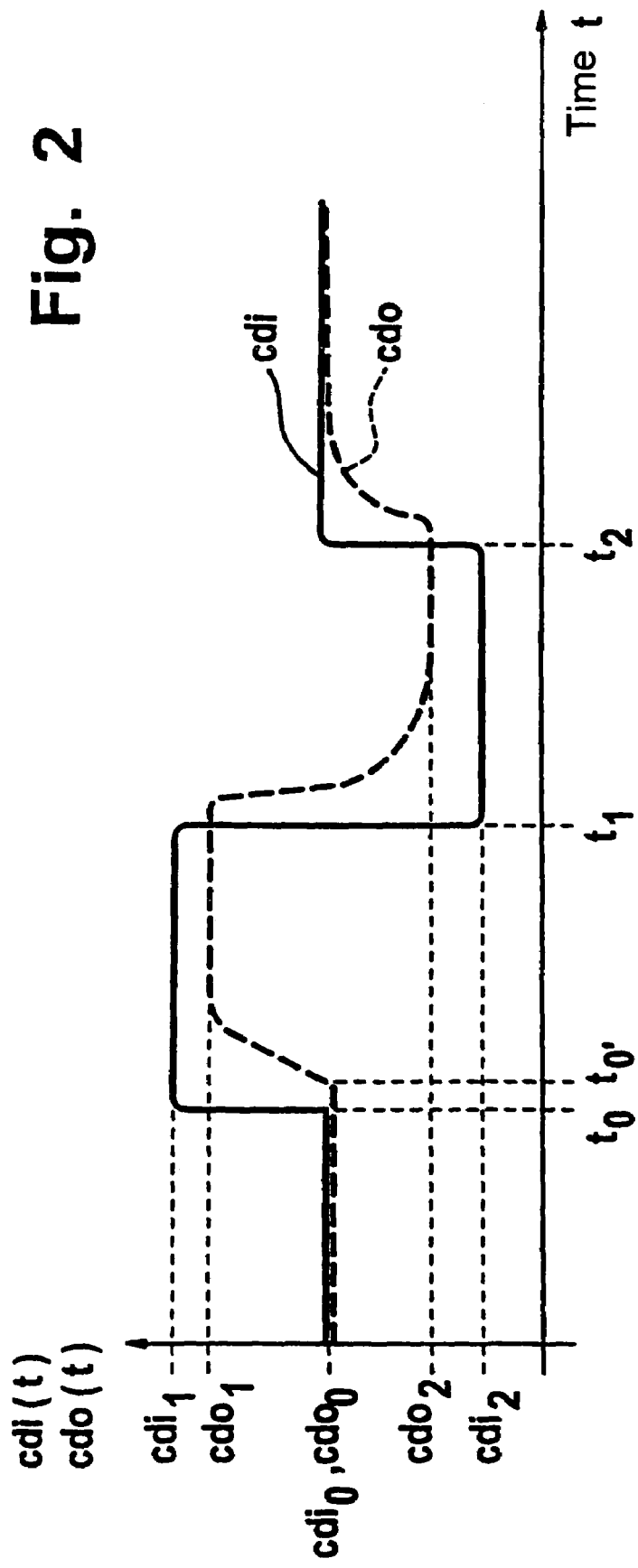

METHOD FOR DETERMINING THE DISTRIBUTION VOLUME OF A BLOOD COMPONENT DURING AN EXTRACORPOREAL BLOOD TREATMENT AND DEVICE FOR CARRYING OUT THE METHOD

The present invention relates to a method for determining the distribution volume of a blood component in the body of an organism, particularly the urea distribution volume, during an extracorporeal blood treatment. In addition, the present invention relates to an apparatus for determining the distribution volume of a blood component in the body of an organism during an extracorporeal blood treatment in conjunction with a device for the extracorporeal blood treatment.

An essential task of the human kidneys is the separation of substances, usually eliminated with urine, from the blood, and the regulation of the water and electrolyte excretion. Hemodialysis represents a treatment method to compensate for dysfunctions of the kidneys with respect to the removal of substances usually eliminated with urine, and the adjustment of the electrolyte concentration in the blood.

During hemodialysis, the blood is conducted in an extracorporeal circuit through the blood chamber of a dialyzer, the blood chamber being separated from a dialyzing-fluid chamber by a semipermeable membrane. A dialyzing fluid containing the blood electrolytes in a specific concentration flows through the dialyzing-fluid chamber. The substance concentration (cd) of the dialyzing fluid corresponds to the concentration of the blood of a healthy individual. During the treatment, the blood of the patient and the dialyzing fluid are conducted past both sides of the membrane, generally in counterflow with a predefined flow rate(Qb and Qd, respectively). The substances usually eliminated with urine diffuse through the membrane from the blood chamber into the chamber for dialyzing fluid, while at the same time, electrolytes present in the blood and in the dialyzing fluid diffuse from the chamber of higher concentration to the chamber of lower concentration. The substance exchange can be additionally influenced by applying a trans-membrane pressure.

To permit optimization of the blood-treatment process, the determination of parameters for the hemodialysis during the extracorporeal blood treatment (in-vivo) is necessary. Of interest is the value for the exchange efficiency of the dialyzer, which is represented by the so-called "clearance" or "dialysance D".

Designated as clearance for a specific substance K is that virtual (calculated) blood volume which is completely freed of a specific substance per minute under defined conditions in the dialyzer. The dialysance D is a further concept for determining the performance of a dialyzer, in which the concentration of the eliminated substance in the dialyzing fluid is taken into account. In addition to these parameters for describing the performance of the dialyzer, other parameters are also important, such as the values for the aqueous component of the blood, the blood volume and the blood input concentration, etc.

The mathematical quantification, using measuring techniques, of the blood-purification process and the determination of the aforesaid parameters of the dialysis are relatively complex. With respect to the computational fundamentals, reference is made to J. A. Sargent, F. A. Gotch: "*Principles and Biophysics of Dialysis*" in: *Replacement of Renal Function by Dialysis*, C. Jacobs, C. M. Kjellstrand, K. M. Koch, J. F. Winchester (editor), Kluwer Academie Publisher, Dordrecht, 1996.

The dialysance, i.e. the clearance can be determined as follows for a given electrolyte, e.g. sodium, at an ultrafiltration rate of zero. The dialysance D is equal to the relationship between the mass transport on the blood side for this electrolyte ($Q_b \times$(cbi-cbo)) and the concentration difference of this electrolyte between the blood and the dialyzing fluid at the respective input of the dialyzer (cbi-cdi).

$$D = Qb \cdot \frac{cbi - cbo}{cbi - cdi} \quad (1)$$

For reasons of mass balance, the following is applicable:

$$Qb \cdot (cbi - cbo) = -Qd \cdot (cdi - cdo) \quad (2)$$

Following from the two equations (1) and (2) indicated above is:

$$D = -Qd \cdot \frac{cdi - cdo}{cbi - cdi} \quad (3)$$

In this context, in (1) through (3):
Qb=effective flow of blood
Qd=flow of dialyzing fluid
cb=substance concentration in the blood
cd=substance concentration in the dialyzing fluid
i=input of the dialyzer
o=output of the dialyzer The effective blood flow is the flow of the blood component in which the substances to be removed are dissolved, i.e. it relates to the (aqueous) solution volume for this substance. Depending on the substance, it can be the plasma water flow or the blood serum flow, i.e. the entire water content in the whole blood. If the whole-blood flow $Q_{Vb}$ is ascertained, then Qb can be determined from $Q_{Vb}$ using a constant factor.

In the event that the ultrafiltration rate Qf is not equal to zero, dialysance D is calculated as follows:

$$D = \left[ Qd \frac{cdo - cdi}{cbi - cdi} \right] \cdot \left[ 1 - \frac{Qf}{Qb} \right] + Qf \quad (4a)$$

The diffusive component of the dialysance $D_{diff}$ is then calculated as follows:

$$D_{diff} = \left[ Qd \frac{cdo - cdi}{cbi - cdi} \right] \cdot \left[ 1 - \frac{Qf}{Qb} \right] \quad (4b)$$

For ionic substances, the Gibb's Donnan coefficient must be taken into account for the blood input concentration. For this, reference is made to the article by Sargent and Gotch cited above. For the sake of simplicity, this correction factor is omitted in the following.

The German patent DE 39 38 662 C2 (EP 0 428 927 A1) describes a method for the in-vivo determination of parameters for the hemodialysis, in which the dialysate-electrolyte transfer is in each case measured for two different dialysate input concentrations. Assuming that the blood input concentration is constant, according to the known method, the dialysance is determined in that the difference is determined between the differences of the dialyzing fluid ion concentration at the input side and the output side of the dialyzer at the instant of the first and second measurement, this is divided by the difference of the dialyzing fluid ion concentration at the input side at the instant of the first measurement and of the second measurement and is multiplied by the dialyzing-fluid flow.

To be able to make a statement about the dialyzing dosage for the hemodialysis, the so-called "Kt/V" parameter is of particular interest. To calculate this parameter, the product of the clearance K and the treatment time t is formed, and is divided by the distribution volume V of the substance to be removed, usually urea.

The treatment time is predefined and therefore known. The clearance for the type of dialyzer used can be gathered from tables, or else can be ascertained online (DE 39 38 662 C2). In principle, the distribution volume of a substance can be determined using a normal dilution measurement in which an exactly measured marker fluid is injected into the patient and its uniform concentration in the blood is measured after a sufficient distribution time. However, this proves to be too costly for a routine process which must be used, for example, three times per week.

Therefore, the distribution volume V is usually ascertained with empirical estimation formulas, into which parameters are entered such as the body size and the weight of the patient to be treated. The value ascertained for V is admittedly very imprecise.

A method is known from WO 98/55166 for determining the mass of a constituent such as urea in the blood, in which the concentration of the constituent in the dialyzing fluid is measured downstream of the dialyzer during the treatment. The mass of the constituent is determined from the change in the concentration as a function of time. The distribution volume should be calculated from the mass of the constituent. It is disadvantageous that the distribution volume is not determined continually, but rather only at the end of a treatment segment.

The object of the present invention is to specify a method which allows rapid and automated determination of the distribution volume of a blood component in the body of an organism during an extracorporeal blood treatment. A further objective underlying the present invention is to provide an apparatus for determining the distribution volume of a blood component in the body of an organism.

This objective is achieved according to the present invention by the features specified in Patent Claims 1 and 10, respectively.

Determination of the distribution volume of a blood component in the body of an organism during an extracorporeal blood treatment is based on the change in a physical or chemical characteristic of the dialyzing fluid in the dialyzing-fluid path during the blood treatment and the measurement of the physical or chemical characteristic of the dialyzing fluid downstream of the dialyzer. The physical or chemical characteristic of the dialyzing fluid is altered in the dialyzing-fluid path upstream from the dialyzer. In this context, the physical or chemical characteristic should be adjusted to physiologically tenable values.

If the change in the characteristic upstream of the dialyzer is known, it is possible to dispense with this measurement. Otherwise the characteristic is measured not only downstream, but also upstream of the dialyzer.

The change in the concentration of the blood component in the blood as a function of time is determined from the physical or chemical characteristic of the dialyzing fluid downstream of the dialyzer. The distribution volume of the substance in the body of an organism is then inferred from the change in the concentration of the blood component in the blood over time.

The physical or chemical characteristic of the dialyzing fluid upstream and downstream of the dialyzer is advantageously the concentration of a substance in the dialyzing fluid upstream and downstream of the dialyzer (dialyzing fluid input concentration and output concentration cdi, cdo). A deviation in the dialyzing fluid input concentration from the blood input concentration cbi leads to a change in the blood input concentration cbi at the dialyzer, since the measured substance shifts to or from the blood side. The distribution volume of this substance in the blood is then inferred from the change in the blood input concentration as a function of time.

To determine the distribution volume of sodium in the blood, preferably the conductivity of the dialyzing fluid is measured as a physical or chemical characteristic. The known conductivity sensors can be used for this purpose.

The urea distribution volume can be inferred from the sodium distribution volume, since the urea distribution volume corresponds essentially to the sodium distribution volume.

After the urea distribution volume is determined, the so-called "Kt/V" parameter can be calculated, in doing which the clearance K can either be ascertained according to the method known from DE 39 38 662 C2, or gathered from corresponding tables for the individual types of dialyzer.

In calculating the distribution volume V, the starting point is initially the following mass balance equation:

$$\int_{t}^{t+\Delta t} Qd * cdi(t') dt' - \int_{t}^{t+\Delta t} (Qd + Qf) * cdo(t') dt' = \quad (5)$$
$$V(t + \Delta t) * cbi(t + \Delta t) - V(t) * cbi(t)$$

Equation (5) represents how the blood concentration cbi changes on the basis of the shift of substances into or out of the blood. If equation (5) is divided by $\Delta t$ and the limiting value $\Delta t \rightarrow \infty$ is then considered, then the integral mass balance according to equation (5) is converted into a differential mass balance:

$$Qd * cdi(t) - (Qd + Qf) * cdo(t) = cbi(i)\frac{dV(t)}{dt} - V(t)\frac{dcbi(t)}{dt} \quad (6)$$

Solved according to dcbi(t)/dt and with dV(t)/dt=-Qf, this yields equation (7):

$$\frac{dcbi}{dt} = \frac{Qd * cdi(t) - (Qd + Qf) * cdo(t) + Qf * cbi(t)}{V(t)} \quad (7)$$

Equation (7) represents the basis for the continuing considerations, it being assumed that the time profile of cdi(t) leads to a change of cbi(t), and the measuring time is conditional upon a sufficient mixture in the blood of the patient.

Equation (7) can be evaluated in widely varying forms. If one assumes cdi(t)=const, as well as cdo(t)≈const and cbi (t)≈const during the measuring phase, which is well fulfilled for the case of a concentration gradient, changing only insignificantly during the measuring time, between the two fluids (i.e. the numerator in (7) changes only insignificantly), then applicable for the period of time t to t+Δt is:

$$V(t) = \frac{(Qd * cdi(t) - (Qd + Qf) * cdo(t) + Qf * cbi(t))\Delta t}{cbi(t + \Delta t) - cbi(t)} \quad (8)$$

The physical or chemical characteristic of the dialyzing fluid upstream of the dialyzer is preferably increased abruptly from an original value to a predefined value, to then be abruptly reduced to a predefined value, whereupon the original value is set again. If the value by which the characteristic is reduced is twice as large as the value by which the characteristic is increased, and the time interval in which the characteristic is increased is equal to the time interval in which the characteristic is reduced, then a symmetrical time profile is present which simplifies the evaluation, since the increase in the characteristic is offset by its decrease. In order not to have to feed to or remove from the patient unnecessary amounts of, for example, sodium during the treatment, the initial value of the characteristic in the dialyzing fluid, which is altered during the measurement, should correspond to the value in the blood.

In the event of unsymmetrical pulses for the two rectangular profiles, the change of the concentration in the blood as a function of time can be exactly calculated by forming a relationship between integral surfaces.

Determining the distribution volume is advantageously even further simplified because during the measurement, the volume of the dialyzing fluid flowing into the dialyzer is equal to the volume of fluid flowing out of the dialyzer. This can be accomplished using the familiar balancing devices. However, it is also possible to ascertain the distribution volume during a continuing ultrafiltration of the blood.

The distribution volume of a blood component in the body of an organism can then also be determined without explicitly ascertaining the change in the concentration of the component in the blood as a function of time.

An exemplary embodiment of a hemodialysis device having an apparatus for determining the urea distribution volume is further described in the following with reference to the drawing, in which:

FIG. 1 shows a simplified schematic representation of a hemodialysis device having the apparatus for determining the urea distribution volume; and FIG. 2 shows the time profile of the dialyzing-fluid input and output concentration.

The apparatus for determining the urea distribution volume can form a separate subassembly. However, it can also be a component of a hemodialysis device, particularly since some components of the apparatus for determining the urea distribution volume are already present in the known dialyzers. In the following, the apparatus for determining the urea distribution volume is described together with the essential components of the dialyzer.

The hemodialysis device has a dialyzer 1 which is separated by a semi-permeable membrane 2 into a blood chamber 3 and a dialyzing-fluid chamber 4. The inlet of the blood chamber is connected to one end of a blood feed line 5 into which a blood pump 6 is switched, while the outlet of blood chamber 3 is connected to the one end of a blood discharge line 7 into which a drip chamber 8 is switched.

The dialyzing-fluid system of the hemodialysis device includes a device 9 for preparing the dialyzing fluid, with which different compositions of the dialyzing fluid (electrolyte dose) can be preselected. Preparation device 9 has a device 17 for altering the substance concentration of the dialyzing fluid, preferably the sodium concentration. A balancing device is also provided which includes two parallel-connected balance chambers that are each subdivided into two balance-chamber halves. For the sake of greater clarity, only the two balance-chamber halves of one balance chamber are shown here. Preparation device 9 is connected to the inlet of first chamber half 11a of balancing device 11 via first section 10a of a dialyzing-fluid feed line 10. Second section 10b of dialyzing-fluid feed line 10 connects the outlet of first balancing-chamber half 11a to the inlet of dialyzing-fluid chamber 4. The outlet of dialyzing-fluid chamber 4 is connected via first section 12a of a dialyzing-fluid discharge line 12 to the inlet of second balancing-chamber half 11b. A dialyzing-fluid pump 13 is switched into first section 12a of dialyzing-fluid discharge line 12. The outlet of second balancing-chamber half 11b is connected to a drain 14 via second section 12b of dialyzing-fluid discharge line 12. Upstream of dialyzing-fluid pump 13, an ultrafiltrate line 15 branches off from dialyzing-fluid discharge line 12 and likewise leads to drain 14. An ultrafiltration pump 16 is switched into ultrafiltrate line 15.

The hemodialysis device also includes a central control unit 18 that is connected via control lines 19 through 22 to blood pump 6, dialyzing-fluid pump 13, ultrafiltration pump 16 and device 17 for altering the sodium concentration of the dialyzing fluid.

During the dialysis treatment, the blood of the patient flows through blood chamber 3, and the dialyzing fluid flows through dialyzing-fluid chamber 4 of dialyzer 1. Since balancing device 11 is switched into the dialyzing-fluid path, only so much dialyzing fluid can flow in via dialyzing-fluid feed line 10 as can flow off via dialyzing-fluid discharge line 12. Fluid can be withdrawn from the patient using ultrafiltration pump 16, the desired ultrafiltration rate being predetermined by the control unit.

Measuring devices 23, 24, respectively, are arranged in feed line 10 and discharge line 12 upstream and downstream of dialyzer 1 for determining the substance concentration of the dialyzing fluid at the input of dialyzer 1 (dialyzing-fluid input concentration cdi) and the substance concentration of the dialyzing fluid at the output of the dialyzer (dialyzing-fluid output concentration cdo). Measuring devices 23, 24 for determining the dialyzing-fluid input and output concentration have conductivity sensors which preferably measure the temperature-corrected conductivity of the dialyzing fluid and thus especially the Na concentration. Instead of conductivity sensors, optical or other sensors, e.g. enzyme sensors, can also be arranged in the dialyzing-fluid path for measuring the dialyzing-fluid input and output concentration.

Arithmetic and evaluation unit 29 is connected via a data line 32 to control unit 18 in order to be able to retrieve flow rates Qb, Qd for blood and dialyzing-fluid pumps 6, 13.

Measuring devices 23, 24 are connected via data lines 25, 26 to a memory unit 27. Memory unit 27 receives the measured values of sensors and stores them in chronological sequence. The measured values are supplied via a data line 28 to an arithmetic and evaluation unit 29 which, in a digital computer (microprocessor), determines the urea distribution volume from the data obtained. The urea distribution volume is displayed on a readout mechanism 30 that is connected via a data line 31 to arithmetic and evaluation unit 29.

The apparatus operates as follows for determining the urea distribution volume:

At the beginning of the measurement, control unit 18 halts ultrafiltration pump 16, so that the ultrafiltration rate is equal to 0. The control unit predefines flow rates Qb and Qd for the flow of the blood and dialyzing fluid.

The dialyzing fluid flows through the dialyzing-fluid chamber with a flow rate Qd predefined by the speed of pump 13, and with dialyzing-fluid input concentration cdi which is set by device 17 and which is detected by measuring device 23 arranged upstream of the dialyzer. The dialyzing-fluid output concentration cdo appearing in response to the dialysis is detected by measuring device 24 arranged downstream of the dialyzer.

Device 17 adjusts a dialyzing-fluid input concentration cdi(t) which has the time profile shown in FIG. 2. Starting from a value $cdi_0$ which is customary for the dialysis treatment and which corresponds or at least comes close to the value $cbi_0$ of the sodium concentration in the blood upstream of the dialyzer, the input concentration is increased to the value $cdi_1$ at point of time $t_0$. At point of time $t_1$, the input concentration is reduced to the value $cdi_2$, to then be set again to the original value $cdi_0$ at point of time $t_2$.

FIG. 2 shows, in dotted lines, the time profile of dialyzing-fluid output concentration cdo(t) appearing downstream of the dialyzer. $cdi_0=cdo_0$ is for t<to. At the end of time interval $t_0<t<t_1$, a value $cdo_1$ appears at the dialyzer output, while at the end of time interval $t_1<t<t_2$, a value $cd_{02}$ appears at the dialyzer output. For $t>t_2$, the dialyzing-fluid output concentration again assumes the value of the dialyzing-fluid input concentration with sufficient accuracy. The dialyzing-fluid input and output concentrations exhibit a symmetrical time profile. The value by which the input concentration is reduced is twice as large as the value by which the input concentration is increased. Time interval $t_1-t_0$ is equal to time interval $t_2-t_1$. The time intervals are regulated such that in each case stable values ensue for cdo. Since the profile is symmetrical, the shift of electrolytes via the membrane of the dialyzer, caused by the first change, is compensated for again.

While the dialyzing-fluid input concentration is changed, the dialyzing-fluid input and output concentrations $cdi_0$, $cdo_0$ within time interval $t<t_0$, $cdi_1$, $cdo_1$ within time interval $t_0<t<t_1$ and $cdi_2$, $cdo_2$ within time interval $t_1<t<t_2$ are measured and stored in memory unit 27. In so doing, it is taken into account that the values for cdo are time-displaced by a delay time $t_d$ with respect to those of cdi.

Since the shift of electrolytes via the dialysis membrane, caused by the first change, is compensated for again in the symmetrical case, the following applies:

$$cdi_0 = cbi_0 = cbi_2 \quad (9)$$

points of time immediately prior to the change of cdi being designated in each case with the subscript as $t_0$, $t_1$ and $t_2$.

The change as a function of time in the blood-input concentration Δcbi is calculated as follows:

$$\Delta cbi = cbi_1 - cbi_0 \quad (10)$$

On condition that an ultra-filtration rate of zero (Qf=0) is set, and assuming that dialysance D does not change during the measurement, arithmetic and evaluation unit 29 calculates Δcbi from the stored values $cdi_0$, $cdo_0$, $cdi_1$, $cdo_1$ and $cdi_2$, $cdo_2$, as well as from the adjusted dialyzing-fluid flow rate Qd on the basis of the following equations:

$$D = \frac{[(cdo_0 - cdi_0) - (cdo_1 - cdi_1)]Qd}{(cbi_0 - cdi_0) - (cbi_1 - cdi_1)} \quad (11)$$

$$D = \frac{[(cdo_1 - cdi_1) - (cdo_2 - cdi_2)]Qd}{(cbi_1 - cdi_1) - (cbi_2 - cdi_2)} \quad (12)$$

$$D = \frac{[(cdo_0 - cdi_0) - (cdo_2 - cdi_2)]Qd}{(cbi_0 - cdi_0) - (cbi_2 - cdi_2)} \quad (13)$$

In these three equations, only D and Δcbi are unknown. The arithmetic unit ascertains these parameters either from two equations hereof, from average values of the respective combinations in pairs, or from a variation calculation which tries to fulfill all three equations as well as possible. In the event D is already known, this can be utilized for further optimization.

After D and Δcbi are ascertained, sodium distribution volume V is calculated in the arithmetic unit according to equation (8), where $\Delta cbi = cbi(t+\Delta t) - cbi(t)$ and $\Delta t = t_1 - t_2$.

For this purpose, arithmetic and evaluation unit 29 reads out the measured values for the dialyzing-fluid input and output concentrations cdi(t), cdo(t), stored during the measurement in their chronological sequence, from memory unit 27. The measuring signals of the conductivity sensors are advantageously sampled, the calculation being carried out by a digital computer.

Assuming that the ascertained sodium distribution volume is essentially equal to the urea distribution volume, the urea distribution volume is determined and displayed on readout mechanism 30. From the known clearance K and treatment time t and the ascertained urea distribution volume V, arithmetic and evaluation unit 29 calculates the "Kt/V" parameter which quantifies the dialyzing dosage. The "Kt/V" parameter is likewise displayed on readout mechanism 30.

For the aforesaid reasons, the change in the dialyzing-fluid input concentration as a function of time should be symmetrical. However, if unsymmetrical pulses are used, it can no longer be assumed that $cbi_0 = cbi_2$. Applicable in this case is:

$$cbi_2 = cbi_0 + \Delta cbi(I_1+I_2)/I_1 \quad (14)$$

$$I_1 = \int_0^{t_1} [cdi(t) - cdo(t+td)] dt \quad (15)$$

$$I_2 = \int_{t_1}^{t_2} [cdi(t) - cdo(t+td)] dt \quad (16)$$

Delay time td is the time after which the dialyzing-fluid output concentration rises after the increase of the dialyzing-fluid input concentration. Delay time td is calculated from the measured time profile of input and output concentrations cdi(t) and cdo(t). It is evident from FIG. 2 that, for the case of a symmetrical profile of cdi, integral surfaces $I_1$ and $I_2$ are nearly identical, which means, as assumed before, $cbi_2 = cbi_0$.

The sodium distribution volume is again calculated in arithmetic and evaluation unit 29 according to the equations (11) through (13), now, however, $cbi_2 = cbi_0 + \Delta cbi(I_1+I_2)/I_1$ being valid. The arithmetic and evaluation unit is provided with integrators for forming integrals $I_1$ and $I_2$.

If ultrafiltration is carried on during the measurement, the sodium distribution volume can only be determined when the values $cbi_{0,1,2}$ for the blood input concentration are known.

To this end, prior to measuring the distribution volume, the blood input concentration cbi can be determined as described in detail in the German patent 39 38 662 C2, to which reference is specifically made. In this context, it is sufficient to ascertain an average value for $cbi_{0,1,2}$.

Arithmetic and evaluation unit 29 now determines $\Delta cbi$ on the basis of the following equations:

$$D_{diff} = \frac{[(cdo_0 - cdi_0) - (cdo_1 - cdi_1)]Qd + [(cbi_1 - cdo_1) - (cbi_0 - cdo_0)]Qf}{\left(1 - \frac{Qf}{Qb}\right)[(cbi_0 - cdi_0) - (cbi_1 - cdi_1)]} \quad (17)$$

$$D_{diff} = \frac{[(cdo_1 - cdi_1) - (cdo_2 - cdi_2)]Qd + [(cbi_2 - cdo_2) - (cbi_1 - cdo_1)]Qf}{\left(1 - \frac{Qf}{Qb}\right)[(cbi_1 - cdi_1) - (cbi_2 - cdi_2)]} \quad (18)$$

$$D_{diff} = \frac{[(cdo_0 - cdi_0) - (cdo_2 - cdi_2)]Qd + [(cbi_2 - cdo_2) - (cbi_0 - cdo_0)]Qf}{\left(1 - \frac{Qf}{Qb}\right)[(cbi_0 - cdi_0) - (cbi_2 - cdi_2)]} \quad (19)$$

$D_{diff}$ represents the diffusive component of the dialysance.

The change as a function of time in the blood-input concentration $\Delta cbi$ is now determined in a similar manner as in the case of $Q_f = 0$ from equations (17) through (19). The sodium distribution volume is then in turn calculated according to equation (8). Arithmetic and evaluation unit 29 thereupon again determines the urea distribution volume from the sodium distribution volume.

However, distribution volume V of a blood component in the body of an organism can also be determined in arithmetic and evaluation unit 29 without explicitly ascertaining the change as a function of time in the concentration of the component in the blood $\Delta cbi$. To this end, device 17 again sets the profile, shown in FIG. 2, for the dialyzing-fluid input concentration cdi(t). The points of time "beginning", "end of the high phase" and "end of the low phase" are again indexed with 0, 1 and 2, respectively.

Dialysance D can be calculated as follows from the dialyzing-fluid input and output concentrations at points of time i, j:

$$D_{i,j} = \left(1 - \frac{cdo_i - cdo_j}{cdi_i - cdi_j}\right)(Qd + Qf) \quad \text{time index } i \neq j \quad (20)$$

The above equation is derived assuming that the plasma-sodium is constant. However, this is not the case because of the salt transfer. If this assumption is not made, then the dialysance is calculated as follows:

$$D_{i,j} = \frac{[(cdo_i - cdi_i) - (cdo_j - cdi_j)]Qd + [(cbi_j - cdo_j) - (cbi_i - cdo_i)]Qf}{(cbi_i - cdi_i) - (cbi_j - cdi_j)} + Qf \quad (21)$$

Analogously, the diffusive component of dialysance $D_{diff}$ for a constant plasma-sodium concentration reads as follows:

$$D_{diff\ i,j} = \frac{[(cdo_i - cdi_i) - (cdo_j - cdi_j)]Qd + (cdo_i - cdo_j)Qf}{\left(1 - \frac{Qf}{Qb}\right)[(cdi_j - cdi_i)]} \quad (22)$$

If the assumption is dropped, the diffusive component of dialysance $D_{diff}$ is calculated as follows:

$$D_{diff\ i,j} = \frac{[(cdo_i - cdi_i) - (cdo_j - cdi_j)]Qd + [(cbi_j - cdo_j) - (cbi_i - cdo_i)]Qf}{\left(1 - \frac{Qf}{Qb}\right)[(cbi_i - cdi_i) - (cbi_j - cdi_j)]} \quad (23)$$

Experiments have shown that, for the step-index profile shown in FIG. 2, equations (20) and (22), respectively, are a good approximation for equations (21) and (23), respectively, for i=1 and j=2.

If the values for the dialysance, which take into account the electrolyte transfer, are now compared to those resulting from a constant blood input concentration cbi, then distribution volume V can be determined.

To determine the distribution volume V, arithmetic and evaluation unit 29 first of all calculates, from the stored measured values, values $D_{0,1}$, $D_{1,2}$ and $D_{diff1,2}$ according to equations (20) and (22) for dialysance D and the diffusive component of the dialysance $D_{diff}$. An ultra-filtration rate Qf of zero is preferably set when acquiring the measurable quantities cdi and cdo.

After determining the above values, the arithmetic and evaluation unit then calculates the distribution volume of the blood component according to the following equation:

$$V(t_1) = \left(\frac{D_{0,1}}{D_{1,2} - D_{0,1}} + 1\right) \cdot \left(\frac{D_{diff\ 1,2}(t_1 - t_0)(cdi_1 - cbi_0)}{cdi_1 - cdi_0}\right) \quad (24)$$

For a constant ultrafiltration rate, distribution volume V can be calculated for any points of time t as follows:

$$V(t) = V(t_1) + Qf(t_1 - 1)$$

The concentration of the component in the blood $cbi_0$ (blood-input concentration) is determined beforehand according to equation (4a) or (4b). Namely, after the arithmetic and evaluation unit has determined the dialysance, the sought-after concentration cbi is the single unknown.

The above equations show that it is not explicitly necessary to determine the change in the blood-input concentration as a function of time. It is sufficient to determine this variable at point of time $t_0$.

Equation (24) was derived assuming that the measurable quantities are recorded only a few minutes after a change in the dialyzing-fluid input concentration, and a shift of electrolytes through the dialyzer membrane proportional to the time ensues. It was further assumed that the recirculation in the fistula of the patient can be disregarded. To expand the validity range as a function of time and to take into account the recirculation, it is also possible to allow for empirically ascertained correction factors $a_1$ for $D_{0,1}$, $D_{1,2}$ and $D_{diff1,2}$ in equation (24). The calculation is then carried out according to the following equation:

$$V(t_1) = \left(\frac{a_1 D_{0,1}}{a_2 D_{1,2} - a_1 D_{0,1}} + 1\right) \cdot \left(\frac{a_3 D_{\text{diff } 1,2}(t_1 - t_0)(cdi_1 - a_4 cbi_0)}{cdi_1 - cdi_0}\right) \quad (25)$$

Experiments have shown that the measuring accuracy is high particularly when the blood and dialyzing-fluid flow Qb, Qd are high.

What is claimed is:

1. A method for determining the distribution volume of a blood component in the body of an organism during an extracorporeal blood treatment, in which the blood to be treated flows in an extracorporeal circuit through the blood chamber of a dialyzer subdivided by a semipermeable membrane into the blood chamber and a dialyzing-fluid chamber, and dialyzing fluid flows in a dialyzing-fluid path through the dialyzing-fluid chamber of the dialyzer, comprising the following method steps:

bringing about a change in the concentration of the blood component in the blood upstream of the dialyzer by a change in the concentration of the blood component in the dialyzing fluid upstream of the dialyzer; and measuring the change in the concentration of the blood component in the dialyzing fluid downstream of the dialyzer which can be attributed to the change in the concentration of the blood component in the blood as a result of the change in the concentration of the blood component in the dialyzing fluid upstream of the dialyzer; and determining the distribution volume V of the blood component from the change in the concentration of the blood component in the dialyzing fluid upstream and downstream of the dialyzer.

2. The method as recited in claim 1, wherein the concentration of the blood component in the dialyzing fluid in the dialyzing-fluid path is measured upstream of the dialyzer.

3. The method as recited in claim 1, wherein the conductivity of the dialyzing fluid is measured as the concentration of the blood component for determining the distribution volume of sodium in the blood.

4. The method as recited in claim 3, wherein the sodium distribution volume is ascertained for determining the distribution volume of urea in the blood, and the urea distribution volume is determined from the sodium distribution volume.

5. The method as recited in claim 4, wherein the urea distribution volume is determined under the assumption that the sodium distribution volume essentially corresponds to the urea distribution volume.

6. A method for determining the distribution volume of a blood component in the body of an organism during an extracorporeal blood treatment, in which the blood to be treated flows in an extracorporeal circuit through the blood chamber of a dialyzer subdivided by a semipermeable membrane into the blood chamber and a dialyzing-fluid chamber, and dialyzing fluid flows in a dialyzing-fluid path through the dialyzing-fluid chamber of the dialyzer, comprising the following method steps:

the concentration of the blood component in the dialyzing fluid is altered in the dialyzing-fluid path upstream of the dialyzer and the concentration of the blood component in the dialyzing fluid is measured downstream of the dialyzer;

the change as a function of time in the concentration of a blood component in the blood upstream of the dialyzer $\Delta cbi$ as a result of the change in the concentration of the blood component in the dialyzing fluid upstream of the dialyzer is determined from the concentration of the blood component in the dialyzing fluid upstream and downstream of the dialyzer after the concentration of the blood component in the dialyzing fluid has been altered; and the distribution volume V of the blood component is determined from the change as a function of time in the concentration of the blood component in the blood.

7. The method as recited in claim 6, wherein the concentration of the blood component in the dialyzing fluid in the dialyzing-fluid path is measured upstream of the dialyzer.

8. A method for determining the distribution volume of a blood component in the body of an organism during an extracorporeal blood treatment, in which the blood to be treated flows in an extracorporeal circuit through the blood chamber of a dialyzer subdivided by a semipermeable membrane into the blood chamber and a dialyzing-fluid chamber, and dialyzing fluid flows in a dialyzing-fluid path through the dialyzing-fluid chamber of the dialyzer, comprising the following method steps:

bringing about a change in the concentration of a blood component in the blood upstream of the dialyzer by a change in a physical or chemical characteristic in the dialyzing fluid upstream of the dialyzer; and measuring the change in the physical or chemical characteristic in the dialyzing fluid downstream of the dialyzer which can be attributed to the change in the concentration of the blood component in the blood; and determining the distribution volume V of the blood component from the change in the physical or chemical characteristic in the dialyzing fluid upstream and downstream of the dialyzer, wherein the physical or chemical characteristic of the dialyzing fluid in the dialyzing-fluid path is increased at a point of time $t_0$ from a predetermined first value $cdi_0$ to a predetermined second value $cdi_1$, is reduced at a point of time $t_1 > t_0$ to a predetermined third value $cdi_2$, and is increased at a point of time $t_2 > t_1$ to a predetermined fourth value $cdi_0$ which is equal to the first value, the value by which the characteristic is increased being half as large as the value by which the characteristic is reduced.

9. The method as recited in claim 8, wherein the time interval $t_1 - t_0$ is equal to the time interval $t_2 - t_1$.

10. The method as recited in claim 8, wherein the change as a function of time in the concentration of a blood component in the blood upstream of the dialyzer $\Delta cbi$ is ascertained from:

the predetermined first value $cdi_0$ of the physical or chemical characteristic of the dialyzing fluid upstream of the dialyzer and the value $cdo_0$ of the characteristic that ensues downstream of the dialyzer, and the predetermined second value $cdi_1$ of the characteristic upstream of the dialyzer and the value $cdo_1$ of the characteristic which ensues downstream of the dialyzer after the increase in the characteristic upstream of the dialyzer to the predetermined second value, and the predetermined third value $cdi_2$ of the characteristic upstream of the dialyzer and the value $cdo_2$ of the characteristic which ensues downstream of the dialyzer after the decrease in the characteristic upstream of the dialyzer to the predetermined third value.

11. The method as recited in claim 10, wherein the dialyzing fluid is balanced such that the volume of the dialyzing fluid flowing into the dialyzer during the measurement is equal to the volume of the dialyzing fluid flowing out of the dialyzer.

12. An apparatus for determining the distribution volume of a blood component in the body of an organism during an extracorporeal blood treatment in conjunction with an extracorporeal blood-treatment device, in which the blood to be treated flows in an extracorporeal circuit through the blood chamber of a dialyzer subdivided by a semipermeable membrane into the blood chamber and a dialyzing-fluid chamber, and dialyzing fluid flows in a dialyzing-fluid path through the dialyzing-fluid chamber of the dialyzer, having
 a device configured to alter the concentration of the blood component in the dialyzing fluid in the dialyzing-fluid path upstream of the dialyzer, and
 a measuring device configured to determine the concentration of the blood component in the dialyzing fluid in the dialyzing-fluid path downstream of the dialyzer,
wherein the apparatus comprises an arithmetic and evaluation configured in such a way that the distribution volume V of the blood component can be determined from a change in the concentration of the blood component in the dialyzing fluid downstream of the dialyzer which can be attributed to the change in the concentration of the blood component in the blood as a result of the change in the concentration of the blood component in the dialyzing fluid upstream of the dialyzer.

13. The apparatus as recited in claim 12, wherein a measuring device is provided for detecting the concentration of the blood component in the dialyzing fluid in the dialyzing-fluid path upstream of the dialyzer.

14. The apparatus as recited in claim 13, wherein the measuring devices for detecting the concentration of the blood component have a conductivity sensor, optical sensor or enzyme sensor arranged in the dialyzing-fluid path downstream and upstream, respectively, of the dialyzer.

15. The apparatus as recited in claim 12, wherein the device for altering the concentration of the blood component is designed in such a way that the concentration of the blood component is increased at a point of time $t_0$ from a predetermined first value $cdi_0$ to a predetermined second value $cdi_1$, is reduced at a point of time $t_1 > t_0$ to a predetermined third value $cdi_2$, and is increased at a point of time $t_2 > \mu t_1$ to a predetermined fourth value $cdi_0$ which is equal to the first value, the value by which the concentration of the blood component is increased being half as large as the value by which the concentration of the blood component is reduced.

16. The apparatus as recited in claim 15, wherein the time interval $t_1 - t_0$ is equal to the time interval $t_2 - t_1$.

17. The apparatus as recited in claim 15, wherein the arithmetic and evaluation unit is designed in such a way that the predetermined first, second and third values $cdi_0$, $cdi_1$, $cdi_2$ of the concentration of the blood component in the dialyzing fluid upstream of the dialyzer and the values $cdo_0$, $cdo_1$, $cdo_2$ of the concentration of the blood component in the dialyzing fluid ensuing downstream of the dialyzer are evaluable for determining the change as a function of time in the concentration of the blood component $\Delta cbi$.

18. The apparatus as recited in claim 12, wherein a balancing device is provided with which the dialyzing fluid can be balanced in such a way that the volume of the dialyzing fluid flowing into the dialyzer during the measurement is equal to the volume of the dialyzing fluid flowing out of the dialyzer.

19. An apparatus for determining the distribution volume of a blood component in the body of an organism during an extracorporeal blood treatment in conjunction with an extracorporeal blood-treatment device, in which the blood to be treated flows in an extracorporeal circuit through the blood chamber of a dialyzer subdivided by a semipermeable membrane into the blood chamber and a dialyzing-fluid chamber, and dialyzing fluid flows in a dialyzing-fluid path through the dialyzing-fluid chamber of the dialyzer, having
 a device configured to alter the concentration of the blood component in the dialyzing fluid in the dialyzing-fluid path upstream of the dialyzer, and
 a measuring device configured to determine the concentration of the blood component in the dialyzing fluid in the dialyzing-fluid path downstream of the dialyzer,
wherein the apparatus comprises an arithmetic and evaluation configured in such a way that the change as a function of time in the concentration of the blood component $\Delta cbi$ in the blood upstream of the dialyzer as a result of the change in the concentration of the blood component in the dialyzing fluid upstream of the dialyzer can be determined from the concentration of the blood component in the dialyzing fluid upstream and downstream of the dialyzer after the concentration of the blood component in the dialyzing fluid has been altered, and the distribution volume V of the blood component can be determined from the change as a function of time in the concentration of the blood component upstream of the dialyzer.

20. The apparatus as recited in claim 19, wherein a measuring device is provided for detecting the concentration of the blood component in the dialyzing fluid in the dialyzing-fluid path upstream of the dialyzer.

21. The apparatus as recited in claim 19, wherein the device for altering the concentration of the blood component is designed in such a way that the concentration of the blood component is increased at a point of time $t_0$ from a predetermined first value $cdi_0$ to a predetermined second value $cdi_1$, is reduced at a point of time $t_1 > t_0$ to a predetermined third value $cdi_2$, and is increased at a point of time $t_2 > t_1$ to a predetermined fourth value $cdi_0$ which is equal to the first value, the value by which the concentration of the blood component is increased being half as large as the value by which the concentration of the blood component is reduced.

22. The apparatus as recited in claim 19, wherein the arithmetic and evaluation unit is designed in such a way that the predetermined first, second and third values $cdi_0$, $cdi_1$, $cdi_2$ of the concentration of the blood component in the dialyzing fluid upstream of the dialyzer and the values $cdo_0$, $cdo_1$, $cdo_2$ of the concentration of the blood component in the dialyzing fluid ensuing downstream of the dialyzer are evaluable for determining the change as a function of time in the concentration of the blood component $\Delta cbi$.

23. The apparatus as recited in claim 19, wherein a balancing device is provided with which the dialyzing fluid can be balanced in such a way that the volume of the dialyzing fluid flowing into the dialyzer during the measurement is equal to the volume of the dialyzing fluid flowing out of the dialyzer.

24. A method for determining the distribution volume of a blood component in the body of an organism during an extracorporeal blood treatment, in which the blood to be treated flows in an extracorporeal circuit through the blood chamber of a dialyzer subdivided by a semipermeable membrane into the blood chamber and a dialyzing-fluid chamber, and dialyzing fluid flows in a dialyzing-fluid path through the dialyzing-fluid chamber of the dialyzer, comprising the following method steps:

a physical or chemical characteristic of the dialyzing fluid is altered in the dialyzing-fluid path upstream of the dialyzer, and the physical or chemical characteristic of the dialyzing fluid is measured downstream of the dialyzer;

the change as a function of time in the concentration of a blood component in the blood upstream of the dialyzer $\Delta cbi$ is determined from the physical or chemical characteristic of the dialyzing fluid upstream and downstream of the dialyzer; and the distribution volume V of the blood component is determined from the change as a function of time in the concentration of a blood component in the blood, wherein the physical or chemical characteristic of the dialyzing fluid in the dialyzing-fluid path is increased at a point of time $t_0$ from a predetermined first value $cdi_0$ to a predetermined second value $cdi_1$, is reduced at a point of time $t_1 > t_0$ to a predetermined third value $cdi_2$, and is increased at a point of time $t_2 > t_1$ to a predetermined fourth value $cdi_0$ which is equal to the first value, the value by which the characteristic is increased being half as large as the value by which the characteristic is reduced.

25. The method as recited in claim 24, wherein the change as a function of time in the concentration of a blood component in the blood upstream of the dialyzer $\Delta cbi$ is ascertained from:

the predetermined first value $cdi_0$ of the physical or chemical characteristic of the dialyzing fluid upstream of the dialyzer and the value $cdo_0$ of the characteristic that ensues downstream of the dialyzer, and the predetermined second value $cdi_1$ of the characteristic upstream of the dialyzer and the value $cdo_1$ of the characteristic which ensues downstream of the dialyzer after the increase in the characteristic upstream of the dialyzer to the predetermined second value, and the predetermined third value $cdi_2$ of the characteristic upstream of the dialyzer and the value $cdo_2$ of the characteristic which ensues downstream of the dialyzer after the decrease in the characteristic upstream of the dialyzer to the predetermined third value.

* * * * *